(12) United States Patent
Gondhalekar et al.

(10) Patent No.: US 10,617,822 B2
(45) Date of Patent: Apr. 14, 2020

(54) VELOCITY-WEIGHTING MODEL PREDICTIVE CONTROL OF AN ARTIFICIAL PANCREAS FOR TYPE 1 DIABETES APPLICATIONS

(71) Applicant: The Regents of the University of California, Oakland, CA (US)

(72) Inventors: Ravi L. Gondhalekar, Cambridge, MA (US); Eyal Dassau, Cambridge, MA (US); Francis J. Doyle, III, Cambridge, MA (US)

(73) Assignee: The Regents of the University of California, Oakland, CA (US)

( * ) Notice: Subject to any disclaimer, the term of this patent is extended or adjusted under 35 U.S.C. 154(b) by 552 days.

(21) Appl. No.: 15/197,236

(22) Filed: Jun. 29, 2016

(65) Prior Publication Data
US 2017/0143899 A1    May 25, 2017

Related U.S. Application Data (60) Provisional application No. 62/185,694, filed on Jun. 28, 2015.

(51) Int. Cl.
| | |
|---|---|
| *A61M 5/172* | (2006.01) |
| *A61M 5/142* | (2006.01) |
| *G16H 20/17* | (2018.01) |
| *G06F 19/00* | (2018.01) |

(52) U.S. Cl.
CPC .......... *A61M 5/1723* (2013.01); *A61M 5/142* (2013.01); *G06F 19/3418* (2013.01); *G06F 19/3456* (2013.01); *G16H 20/17* (2018.01); *A61M 2005/14208* (2013.01); *A61M 2230/201* (2013.01)

(58) Field of Classification Search
CPC .. A61M 2005/14208; A61M 2230/201; A61M 5/142; A61M 5/1723; G06F 19/00; G06F 19/3418; G06F 19/3456; G06Q 10/00; G16H 20/17
See application file for complete search history.

(56) References Cited

U.S. PATENT DOCUMENTS

| | | | | |
|---|---|---|---|---|
| 10,332,633 | B2* | 6/2019 | Duke | G16H 20/17 |
| 2014/0100435 | A1* | 4/2014 | Duke | A61B 5/7275 600/365 |
| 2014/0180240 | A1* | 6/2014 | Finan | A61M 5/1723 604/504 |
| 2015/0273147 | A1* | 10/2015 | Duke | A61M 5/1723 604/504 |

* cited by examiner

*Primary Examiner* — Quynh-Nhu H. Vu
(74) *Attorney, Agent, or Firm* — Richard Aron Osman (57) ABSTRACT

Methods, devices, algorithms, and systems controlling insulin delivery employ velocity-weighting. Predicted glucose outcomes are penalized with a cost modulated by a factor that is a function of the glucose velocity, wherein glucose outcomes are penalized increasingly less for increasingly negative glucose velocities, when glucose level is high, and/or wherein a hyperglycemic glucose value that is already converging to the euglycemic zone results in less corrective action by the controller than were the hyperglycemic state steady.

18 Claims, 7 Drawing Sheets
(7 of 7 Drawing Sheet(s) Filed in Color)

VELOCITY-WEIGHTING MODEL PREDICTIVE CONTROL OF AN ARTIFICIAL PANCREAS FOR TYPE 1 DIABETES APPLICATIONS

This invention was made with government support under Grant Numbers DP3DK094331 and RO1DK085628 awarded by the National Institutes of Health (NIH). The government has certain rights in the invention.

INTRODUCTION

Type 1 Diabetes Mellitus (T1DM) is a metabolic autoimmune disease characterized by the destruction of the pancreas' beta cells, and results in the body being incapable of producing insulin, a hormone that facilitates the absorption of glucose from the blood-stream into many types of cell, and that participates in the endocrine feedback loop that regulates the liver's release/removal of glucose into/from the blood-stream. People with T1DM require the delivery of insulin into their blood-stream from an external source, and tend to suffer great difficulty maintaining healthy blood-glucose levels. Hypoglycemia has very near-term consequences and may result in, e.g., dizziness or disorientation if mild, fits or unconsciousness if serious, and coma or death in severe cases. In contrast, a hyperglycemic state has few consequences if it is brief. However, a blood-glucose level that is high on average over long periods of time may result in a variety of health problems, e.g., cardiovascular disease, kidney failure, and retinal damage, possibly many years down the line.

The ultimate application of this work is an Artificial Pancreas (AP) for the automated delivery of insulin to people with T1DM [1,2,3]. In particular the subcutaneous-subcutaneous AP scheme is developed wherein an AP where insulin delivery (control input) is performed by a Continuous Subcutaneous Insulin Infusion (CSII) pump, and glucose sensing (output measurement for feedback) is based on a Continuous Glucose Monitor (CGM) [4]. A crucial element of any fully automated AP is a feedback control law that performs algorithmic insulin dosing that is effective and safe. For example, glucose controllers based on Model Predictive Control (MPC) [5,6,7,8,9] or proportional-integral-derivative control [10,11] have been proposed. We have been focusing increasingly on developing zone-MPC strategies [12,13,14], whereby blood-glucose levels are controlled with respect to the inclusion within a target zone, rather than to track a singular set-point. This has proven effective in real-life operation of the controller for two reasons. First, there is generally a significant plant-model mismatch due to the large inter- and intra-subject variability of humans' physiology. Second is that the feedback signals, an estimate of the blood-glucose level provided every 5 minutes by a CGM, suffers large errors and delays, both of which have time-varying properties and have proven difficult to model and correct for. The use of zone-MPC provides robustness against excessively responding to noise in the state estimate when the blood-glucose level is estimated to be within the target zone.

As is typical in MPC [15,16], the cost functions usually employed in an AP penalize deviations of the glucose outputs, i.e., differences between predicted glucose levels and the set-point, or, in the case of zone-MPC, distances to the target zone. With no plant-model mismatch and a long prediction horizon that may, as it frequently does in MPC, lead to effective control. However, an AP inevitably operates with large plant-model mismatch, and in practice long prediction horizons do not yield useful predictions. We use a 45 minute prediction horizon, which is considerably shorter than a hyperglycemic excursion due to a large meal (up to 8 hours if unannounced). Furthermore, there are long delays associated with CGM sensing and CSII delivery. The result of using a standard quadratic output cost function is an AP that continues to drive insulin delivery even after the measured peak of a hyperglycemic excursion has been reached, when predicted glucose levels may already be steadily converging to the target zone, driven by past insulin delivery. The controller's goal is to accelerate the arrival of the glucose value within the target zone; this is frequently achieved, but often with the undesirable consequence of controller-induced hypoglycemia due to insulin over-delivery. The solution is typically to de-tune the controller, such that insulin delivery is conservative both on the "uphill" and "downhill" leg of a hyperglycemic excursion, resulting in higher glucose peaks and more time spent outside the target zone.

Here we disclose a velocity-weighting mechanism in the MPC cost function, such that a predicted zone excursion is penalized taking into account both its value and also the rate of change of the blood-glucose trajectory. The disclosed mechanism provides the control designer some new degrees of freedom, and facilitates a somewhat decoupled design of the AP's response during the uphill verses the downhill leg of a hyperglycemic excursion. The goal is to deliver more insulin earlier during an excursion, towards the start of the uphill leg, and allow the controller to deliver less on the downhill leg. In related work [17] we proposed to add a "velocity-penalty" term to the cost function, resulting in more aggressive delivery during uphill travel, directly based on the rate of change of predicted glucose levels. This added term allows an otherwise conservative controller to give an "extra kick" when the glucose trajectory is rising, but the mechanism does not actively allow the controller to "back off" when the trajectory is falling. The velocity-weighting mechanism proposed here serves this latter purpose; instead of penalizing output values using a fixed cost, and further instead of penalizing the glucose velocity directly, the proposed mechanism penalizes the output values based on a weight that is a function of the velocity. As the glucose velocity decreases, by choosing the cost to smoothly converge to zero the MPC cost function is increasingly dominated by the input cost, and actively disregards the output cost. The optimized insulin delivery command then converges as desired to the input's set-point, which is the subject's basal infusion rate.

State-dependent, piece-wise linear/quadratic cost functions are standard practice in hybrid-MPC strategies and result in integer-programming problems. The disclosed approach is distinct and smoothly modulates a quadratic (could include linear) cost based on the velocity (i.e., state). Smoothness allows the resulting optimization problem to be solved via a sequence of Quadratic Programming (QP) problems.

SUMMARY OF THE INVENTION

The invention provides methods, devices, algorithms, and systems for velocity-weighting control of insulin delivery.

In one aspect the invention provides a method of velocity-weighting control of an artificial pancreas for type 1 diabetes applications comprising: penalizing predicted glucose outcomes with a cost modulated by a factor that is a function of the glucose velocity, wherein glucose outcomes are penalized increasingly less for increasingly negative glucose velocities, when glucose level is high, and/or wherein a hyperglycemic glucose value that is already converging to the euglycemic zone results in less corrective action by the controller than were the hyperglycemic state steady.

In another aspect the invention provides a method of Model Predictive Control (MPC) for the closed-loop operation of an Artificial Pancreas (AP) to treat type 1 diabetes mellitus comprising a velocity-weighting mechanism, integrable within an MPC problem's cost function, wherein predicted hyperglycemic blood-glucose excursions are penalized based on the predicted blood-glucose levels' rates of change, wherein the method provides for independently shaping the AP's uphill versus downhill responses to hyperglycemic excursions.

In another aspect, the invention provides a method of controlling insulin delivery comprising:

(a) combining velocity-weighting, which reduces the occurrence of controller induced hypoglycemia, and velocity-penalties, which yield more effective hyperglycemia correction;

(b) employing asymmetric input cost functions which improve safety by allowing a controller to attenuate insulin delivery more easily, and velocity-weighting cost functions which help prevent controller induced hypoglycemia by strategically reducing the controller's aggressiveness when a hyperglycemic state is in the process of correction; or (c) using velocity-weighting to impart control that is aggressive on the uphill leg of a hyperglycemic excursion, but conservative on the downhill leg, wherein the quadratic cost used to penalize the glucose deviation is velocity-dependent, wherein the quadratic cost parameter itself is a function of the rate of change of the glucose output.

The disclosed methods may be implemented in a model predictive control (MPC) algorithm of an artificial pancreas to treat type 1 diabetes mellitus incorporable into a device, strategy, or further algorithm that controls insulin delivery to type 1 diabetics, based on blood glucose measurement feedback, e.g., in insulin pumps, continuous glucose monitoring systems, or an artificial pancreas.

The disclosed methods may be operatively combined with:

(a) a continuous glucose monitor (CGM) sensor;
(b) a state-feedback control system; and/or
(c) an alarm or notification system.

The invention also provides a controller programmed to implement a disclosed method, and use of such controller to control insulin delivery for treating type 1 diabetes mellitus.

In another aspect the invention provides a drug delivery system comprising a controller programmed to implement a disclosed method, a status monitoring system, a drug pump or metering system, and optionally, a drug (e.g., insulin) to be delivered.

In another aspect the invention provides a method for model predictive control (MPC) of an artificial pancreas to treat Type 1 diabetes mellitus incorporating a disclosed method.

The various aspects may be practiced or implemented in additional embodiments, including methods, devices, algorithms and drug directing systems essentially as described herein, and all combinations of the recited particular embodiments.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee FIG. 1. IOB decay curves from [18] and used in IOB constraints in [20].

DESCRIPTION OF PARTICULAR EMBODIMENTS OF THE INVENTION

A key component in a successful artificial pancreas system designed to maintain the blood glucose concentrations of people with type 1 diabetes mellitus within the euglycemic zone (80-140 mg/dL) is the control algorithm that automatically directs the delivery of insulin to be administered to a subject with type 1 diabetes. There are many varieties of control algorithm; this invention is of relevance to classes of control strategies based on "model predictive control" (MPC) algorithms. These are real-time optimization based controllers that perform optimal insulin delivery with respect to predicted glucose outcomes and an objective function, also known as a cost function.

The present invention improves the safety of an artificial pancreas device by strategically reducing the risk of insulin over-delivery and the resulting controller-induced hypoglycemia. This is achieved by employing a novel structure of objective function for use with the MPC optimization. Instead of a fixed cost, e.g., a linear or quadratic function as is typically used in MPC, for penalizing predicted glucose outcomes, the invention employs a cost that may be linear or quadratic (or more general even), but is modulated by a factor that is a function of the glucose velocity, i.e., the rate of change of blood glucose concentration. Specifically, glucose outcomes are penalized increasingly less for increasingly negative glucose velocities, when the glucose level is high. Thus, a stubbornly high glucose value results in a more aggressive controller than an equally high glucose value on a trajectory that is falling. Furthermore, a glucose descent of increasing speed causes the controller to be increasingly conservative, to a certain limit.

The invention functions by appending to the typical cost employed in the MPC objective function, be that a linear, quadratic, or more general, cost structure, a further term that is multiplied with the part of the cost incurred by hyperglycemic glucose predictions.

This term is a so-called "velocity-weighting" function that is a design parameter and modulates the typical MPC control behavior based on the glucose velocity (rate of change) at the point in predicted time that is being penalized. Setting the velocity-weighting function to unity for all glucose velocities results in the standard MPC controller. The invention functions by designing the velocity weighting function to not be unity in a well-specified way to converge to zero as the predicted glucose velocity becomes increasingly negative. Thus a hyperglycemic glucose value that is already converging to the euglycemic zone results in less corrective action by the controller than were the hyperglycemic state steady. The resulting MPC problem is no longer a linear, quadratic, or more general convex program as is typically employed in MPC. The invention computes an optimal solution to the resulting optimization problem by a method similar to sequential quadratic programming.

The invention provides a model predictive control algorithm that can be incorporated into a device, strategy, or further algorithm that controls insulin delivery to type 1 diabetic people, based on blood glucose measurement feedback, e.g., in insulin pumps, continuous glucose monitoring systems, or an artificial pancreas. This invention can be used to improve the capabilities of an artificial pancreas that uses model predictive control based on blood glucose measurements as feedback, in maintaining the blood glucose levels of people with type 1 diabetes mellitus within euglycemic range (80-140 mg/dL).

The invention was validated on the University of Virginia/Padova FDA accepted metabolic simulator, and on historical trial data from clinical studies unrelated to the invention, and has been implemented in an experimental artificial pancreas device/system.

Example: Velocity-Weighting to Prevent Controller-Induced Hypoglycemia in MPC of an Artificial Pancreas to Treat T1DM I. The design of a Model Predictive Control (MPC) strategy for the closed-loop operation of an Artificial Pancreas (AP) to treat type 1 diabetes mellitus is developed. We disclose a velocity-weighting mechanism, integrable within an MPC problem's cost function, that facilitates penalizing predicted hyperglycemic blood-glucose excursions based on the predicted blood-glucose levels' rates of change. The method provides the control designer some freedom for independently shaping the AP's uphill versus downhill responses to hyperglycemic excursions; of particular emphasis is the downhill response. The proposal tackles the dangerous issue of controller-induced hypoglycemia following large hyperglycemic excursions, e.g., after meals, that results in part due to the large delays of subcutaneous glucose sensing and subcutaneous insulin infusion—the case considered here. The efficacy of the proposed solution is demonstrated using the University of Virginia/Padova metabolic simulator with both unannounced and announced meal scenarios.

II. MPC DESIGN

A. Insulin-Glucose Transfer Function

The insulin-glucose model of [13] is employed here and is summarized as follows. The model is a discrete-time, Linear Time-Invariant (LTI) system with sample-period T=5 [min]. The time step index is denoted by i. The scalar plant input is the administered insulin bolus $u_{IN,i}$ [U] delivered per sample-period, and the scalar plant output is the subject's blood-glucose value $y_{BG,i}$ [mg/dL]. The plant is linearized around a steady-state that is assumed to be achieved by applying the subject-specific, time-dependent basal input rate $u_{BASAL,i}$ [U/h], and is assumed to result in a steady-state blood-glucose output $y_s$=110 [mg/dL].

The LTI model's input $u_i$ and output $y_i$ are defined as:

$$u_i := u_{IN,i} - u_{BASAL,i} \frac{T}{60 \text{ min/h}}$$

$$y_i := y_{BG,i} - y_s.$$

We denote by $z^{-1}$ the backwards shift operator, by $Y(z^{-1})$ and $U(z^{-1})$ the z-transform of the time-domain signals of input $u_i$ and output $y_i$, respectively. The transfer characteristics from u to y are described by $$\frac{Y(z^{-1})}{U(z^{-1})} = \frac{1800Fc}{u_{TDI}} \cdot \frac{z^{-3}}{(1-p_1 z^{-1})(1-p_2 z^{-1})^2} \qquad (1)$$

with poles $p_1$=0.98, $p_2$=0.965, a so-called safety factor F=1.5 (unitless, can be personalized, but fixed to 1.5 herein), the subject specific total daily insulin amount $u_{TDI}$ [U] (positive scalar), and where the constant $$c := -60(1-p_1)(1-p_2)^2$$

is employed to set the correct gain, and for unit conversion. The 1800 term is from the "1800 rule" to estimate blood-glucose decrease w.r.t. delivering rapid-acting insulin [18].

B. State-Space Model

The state-space realization of (1) used here is $$x_{i+1} = Ax_i + Bu_i \qquad (2a)$$

$$y_i = C_y x_i \qquad (2b)$$

$$v_i = C_v x_i \qquad (2c)$$

$$A := \begin{bmatrix} p_1 + 2p_2 & -2p_1 p_2 - p_2^2 & p_1 p_2^2 \\ 1 & 0 & 0 \\ 0 & 1 & 0 \end{bmatrix} \in \mathbb{R}^{3 \times 3}$$

$$B := \frac{1800Fc}{u_{TDI}} [1 \ 0 \ 0] \in \mathbb{R}^3$$

$$C_y := [0 \ 0 \ 1] \in \mathbb{R}^{1 \times 3}$$

$$C_v := [0.1 \ 0 \ -0.1] \in \mathbb{R}^{1 \times 3}$$

The triple (A, B, $C_y$) describes (1). Note that, without plant-model mismatch, $x_i := [y_i \ y_{i+1} \ y_{i+2}]^T$. The second output matrix, $C_v$, was chosen such that the output $v_i$ of (2c) provides an estimate of the average, over the next 2T=10 min, rate of change of blood-glucose level, in units mg/dL/min. The output $v_i$ is henceforth termed the "velocity" and is employed in the proposed velocity-weighting. This notion of the velocity output was first introduced in [17].

C. State-Estimation

An estimate of the state is provided at each step i by a linear state-estimator (see, e.g., [19]). For brevity the state-estimator details are omitted, thus we make the simplifying assumption that the state $x_i$ is available for all i. No notational distinction is made between the actual and estimated state, because the state x of model (2) can only be estimated.

D. Blood-Glucose Target Zone

In this work the blood-glucose target zone, i.e., the blood-glucose values for which only the basal-rate is delivered, is the range [80,140] mg/dL, the same as in [12,13]. For simplicity the zone is time-invariant, in contrast to [14]. The (signed) zone-excursion $Z \mathbb{R} \to \mathbb{R}$ is defined as:

$$Z(y) := \arg\min_{\alpha \in \mathbb{R}} \{\alpha^2 | y + y_s - \alpha \in [80,140]\}.$$

E. Insulin Delivery Constraints

At each step i the controller must enforce the constraint $$0 \leq u_i + u_{BASAL,i} \leq u_{MAX}, \quad (3)$$

where $u_{MAX}$ denotes the maximum bolus size the CSII pump of choice is capable of delivering. In this work we choose $u_{MAX}=25$ [U]. Note that this bolus size is so large it is highly unlikely to ever be commanded by the controller.

Figure 1:
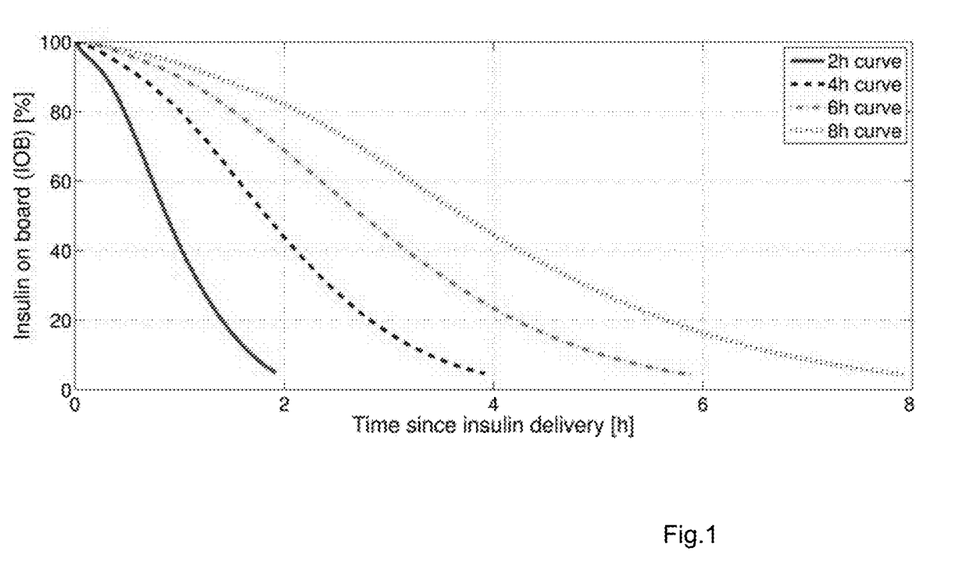

Insulin delivery is further subject to an Insulin On Board (IOB) constraint—a constraints based on the insulin delivery history, preventing over-delivery when much insulin was recently delivered, e.g., after a meal-bolus. The notion of IOB constraints is taken from [20] and modified slightly; reasons for the modification are not explained here, but the stated IOB constraints have proven themselves effective in clinical trials. Let vectors $\theta_l \in \mathbb{R}^{96}$ for $l=2, 4, 6,$ and 8 denote the 2, 4, 6, and 8 hour, respectively, decay curves depicted in FIG. 1. The curves are sampled at $T=5$ min intervals, and each curve is eight hours in duration, padded with trailing zeros when necessary: $8h/T=96$. The decay curve $\theta_i$ applicable at step i depends on the current glucose value $y_{BG,i}$:

$$\theta_i := \begin{cases} \theta_2 & \text{if } y_{BG,i} > 300 \\ \theta_4 & \text{if } y_{BG,i} \in (200, 300] \\ \theta_6 & \text{if } y_{BG,i} \in (140, 200] \\ \theta_8 & \text{otherwise.} \end{cases}$$

Let $\Lambda_{BASAL} \in \mathbb{R}^{96}$ denote the 8 hour history of the linearized insulin infusion commands, but setting to zero the value at any step were a manual meal-bolus was delivered. Further denote by $\Lambda_{MEAL} \in \mathbb{R}^{96}$ the 8 hour history of meal-boluses, by $\Theta \in \mathbb{R}$ the computed amount of IOB present, by $\Gamma \in \mathbb{R}$ the required amount of IOB that depends on current blood-glucose levels, and by $C_f$ [(mg/dL)/U] the patient's so-called correction-factor. At each time step i the IOB upper bound $u_{IOB}$ is subsequently given by $$u_{IOB,i} := \begin{cases} \Theta_i - \Gamma_i & \text{if } \Theta_i > \Gamma_i \\ 0 & \text{otherwise} \end{cases} \quad (4)$$

$$\Theta_i := \theta_i^T \Lambda_{BASAL,i} + \theta_4^T \Lambda_{MEAL,i}$$

$$\Gamma_i := (y_{BG,i} - y_s)/C_f.$$

It holds that $u_{IOB} \geq 0$, and $U_{IOB}=0$ implies the controller delivers no more than $u_{BASAL,i}$ in absolute terms. Thus, after a large bolus the insulin delivery is temporarily constrained to the basal rate, but note that the IOB constraint cannot constrain insulin delivery to below the basal rate.

F. MPC Problem

For MPC background the reader is referred to [15,16]. We denote by $\mathbb{Z}_+$ the set of positive integers, by $\mathbb{Z}_a^b$ the set of consecutive integers $\{a, \ldots, b\}$, by u, x, y, v the predicted input u, state x, glucose output y, and velocity output v, respectively, by $N_y \in \mathbb{Z}$ the prediction horizon, by $N_u \in \mathbb{Z}_1^{N_y}$ the control horizon, by $\hat{R}, \check{R} \in \mathbb{R}_{>0}$ weighting coefficients for non-negative and non-positive control inputs, respectively, and by $Q: \mathbb{R} \to \mathbb{R}_{>0}$ a velocity-weighting function. Then, MPC performs closed-loop control by applying at each step i the first element $u^*_0$ of the optimal, predicted control input trajectory $\{u^*_0, \ldots, u^*_{N_u-1}\}$, characterized as follows.

MPC Problem: Determine $$\{u^*_0, \ldots, u^*_{N_u-1}\} := \arg\min_{\{u_0, \ldots, u_{N_u-1}\}} J(x_i \{u_0, \ldots, u_{N_u-1}\})$$

with cost function $$J(\cdot) := \Sigma_{k=1}^{N_y}[Q(v_k)\hat{z}_k^2 + \check{z}_k^2] + \Sigma_{k=0}^{N_u-1}[\hat{R}\hat{u}_k^2 + \check{R}\check{u}_k^2] \quad (5)$$

and subject to $$x_0 := x_i \quad (6a)$$

$$x_{k+1} := Ax_k + Bu_k \forall k \in \mathbb{Z}_0^{N_y-1} \quad (6b)$$

$$y_k := C_y x_k \forall k \in \mathbb{Z}_0^{N_y} \quad (6c)$$

$$v_k := C_v x_k \forall k \in \mathbb{Z}_0^{N_y} \quad (6d)$$

$$0 \leq u_k + u_{BASAL,(i+k)} \leq u_{MAX} \forall k \in \mathbb{Z}_0^{N_u-1} \quad (6e)$$

$$u_k \leq u_{IOB,i} \forall k \in \mathbb{Z}_0^{N_u-1} \quad (6f)$$

$$u_k := 0 \ \forall k \in \mathbb{Z}_{N_u}^{N_y-1} \quad (6g)$$

$$\hat{z}_k := \max(Z(y_k), 0) \forall k \in \mathbb{Z}_0^{N_y} \quad (6h)$$

$$\check{z}_k := \min(Z(y_k), 0) \forall k \in \mathbb{Z}_0^{N_y} \quad (6i)$$

$$\hat{u}_k := \max(u_k, 0) \forall k \in \mathbb{Z}_0^{N_u-1} \quad (6j)$$

$$\check{u}_k := \min(u_k, 0) \forall k \in \mathbb{Z}_0^{N_u-1}. \quad (6k)$$

Eqs. (6a)-(6d) enforce the prediction dynamics of model (2), initialized to the current state. Eqs. (6e) and (6f) enforce input constraint (3) and (4), respectively, across the control horizon. Eq. (6g) implies that beyond the control horizon exactly the basal-rate is delivered. Eqs. (6h) and (6i) provide upper and lower zone deviations to penalize in (5), respectively, and facilitate an asymmetric penalization of the zone deviation. Eqs. (6j) and (6k) provide the positive and negative deviations of the input u from the basal-rate, respectively, and again facilitate an asymmetric cost function. Asymmetric input cost functions were proposed in [17] and have proven effective in clinical trials.

G. Pump-Discretization

At each step i, after the solution to the MPC Problem above is computed, the determined $u^*_0$ is rounded down to the nearest integer multiple of the CSII pump-discretization of 0.05 U. The portion rounded down is added at the next step in a so-called carry-over scheme. Other than that, no post-processing of the control command is performed.

H. Velocity-Weighting Function Q(•)

Figure 2:
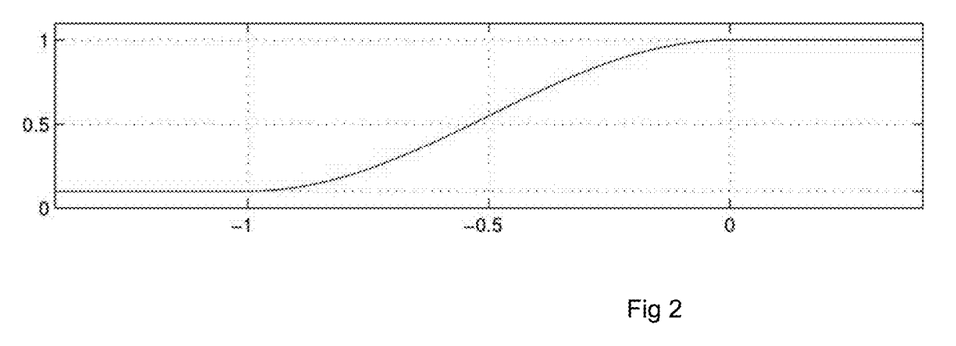
FIG. 2. Velocity-weighting function (7).

One contribution of our work is to consider velocity-weighting functions $Q(\cdot)$ that are more general than $(v)=1$ $\forall v \in \mathbb{R}$. If $Q(v)$ is unity for all velocities v then the output cost function is that of standard (zone) MPC; the cost of a zone deviation is then both invariant and symmetric, and the resulting cost function (5) is that employed in [17], but without the velocity-penalty proposed in [17]. In this work we use the velocity-weighting function of (7), depicted in FIG. 2, with $10^{-6}=\varepsilon \ll 1$. It has the desired features that $Q(v)=1$ if $v>0$ (i.e., we obtain the standard MPC solution for non-negative velocities), $Q(v)=\varepsilon \ll 1$ if $v<-1$ (i.e., the zone excursion is effectively not penalized at all for steep negative glucose velocities, resulting in the input's set-point being commanded), and with a smooth transition when $-1 \leq v \leq 0$, allowing the MPC solution to slowly converge to the input's set-point as the velocity becomes increasingly negative. We require $\varepsilon > 0$ to result in a well-posed problem.

$$Q(v) := \begin{cases} 1 & \text{if } v \geq 0 \\ \varepsilon & \text{if } v \leq -1 \\ \frac{1}{2}[\cos(v\pi)(1-\varepsilon) + (1+\varepsilon)] & \text{otherwise} \end{cases} \quad (7)$$

If $Q(\bullet)$ is any positive constant then the MPC Problem can be cast as a continuous, strictly-convex QP. If $Q(\bullet)$ is a more general function then the MPC Problem is not a QP, but under mild assumptions of continuity and smoothness of $Q(\bullet)$ a solution to the MPC Problem can be obtained by sequential quadratic programming.

III. Examples and Discussion

A. Simulation Setup

In this section the disclosed velocity-weighting MPC, utilizing the velocity-weighting function depicted in FIG. 2, is compared to "standard MPC" with $Q(v)=1$ using the University of Padova/Virginia Food and Drug Administration (FDA) accepted metabolic simulator [21], based on the following scenario. Simulations start at midnight, are 20 hours in duration, and a 90 gram carbohydrate meal is consumed at 04:00. The parameters of both the simulator and controller are time-invariant, thus the time of day of meal consumption is irrelevant. We consider either unannounced meals, where the meal-disturbance is rejected based on feedback only, or announced meals, where a meal-bolus is delivered at the start of meal-ingestion, and the bolus size is optimal with respect to the in-silico subject's parameters. The controller parameters are $N_y=9$ (i.e., 45 minute prediction horizon), $N_u=5$ (i.e., 25 minute control horizon), $\hat{R}=7000$, $\check{R}=100$. The feedback signal for control is the simulator's CGM signal, but with no additive noise. CGM noise is omitted in the cases presented in this work in order to demonstrate the velocity-weighting action of the disclosed controller; without noise the differences between velocity-weighting MPC and standard MPC occur only after the peak of the hyperglycemia excursion. However, cases with CGM noise, and also with more challenging scenarios, were tested, and our overall conclusions hold for these cases also.

B. Single Subject Examples

Figure 3:
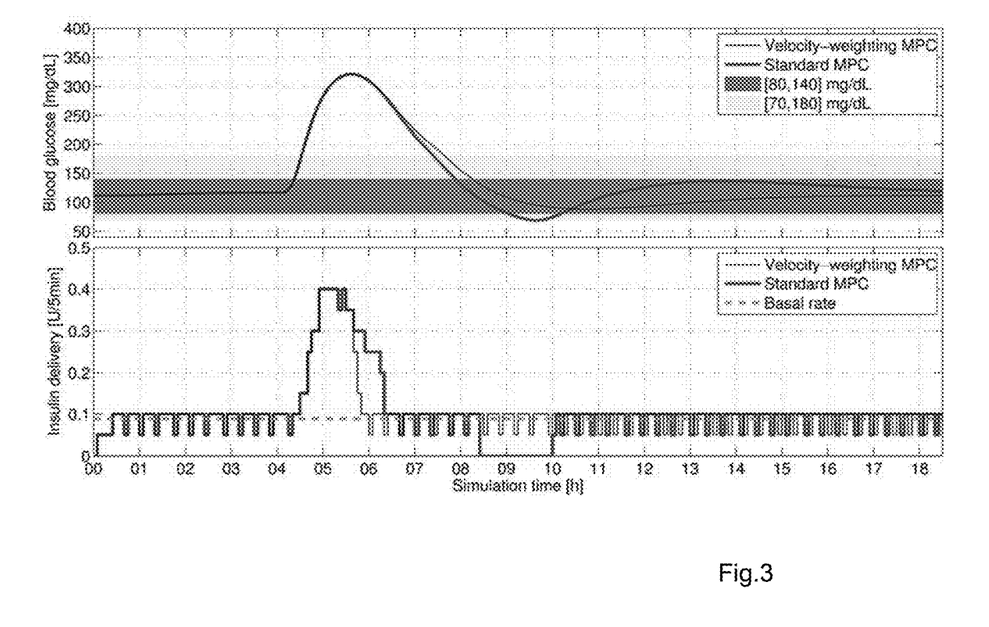
FIG. 3. Unannounced meal. In-silico subject #12 of 100.

A simulation example of the situation the disclosed velocity-weighting MPC is targeted at is depicted in FIG. 3. The use of standard MPC results in significant insulin infusion after the peak, when blood-glucose values are already descending towards the zone, causing hypoglycemia at 09:30. The controller suspends the pump from about 08:30 until 10:00, and after some rebound glucose stabilizes. In contrast, the proposed velocity-weighting MPC reduces insulin infusion to the basal-rate soon after the peak is reached, slowing the descent. No hypoglycemia is induced, and after 06:00 the controller delivers the basal-rate continuously, with no pump-suspension required, and no associated glucose rebound.

Figure 4:
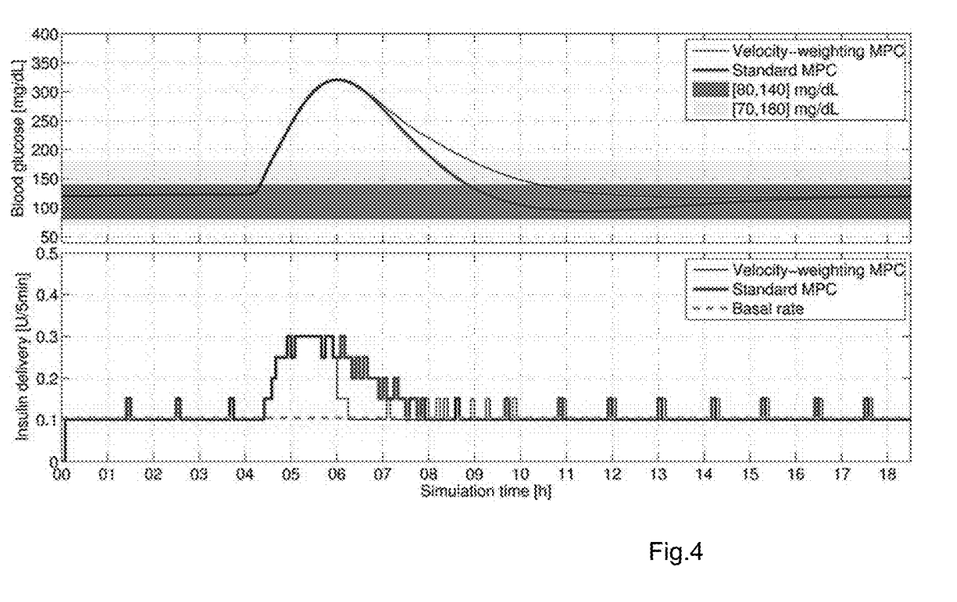
FIG. 4. Unannounced meal. In-silico subject #8 of 100.

In the example of FIG. 4 standard MPC does not induce hypoglycemia, but velocity-weighting MPC again effects an obvious reduction in insulin delivery during the descent. This example demonstrates a possible drawback of the proposed strategy: For some subjects the proposal results in a more sluggish return to the zone, and more time spent in hyperglycemia. However, for such subjects a more aggressively tuned controller, i.e., smaller $\hat{R}$, in combination with the proposed velocity-weighting MPC strategy, delivers more insulin during the ascent, possibly reducing the peak glucose value and time in hyperglycemia. In this disclosure the value of $\hat{R}$ is fixed in order to elucidate the differences in glucose outcomes induced by only the proposed velocity-weighting.

Figure 5:
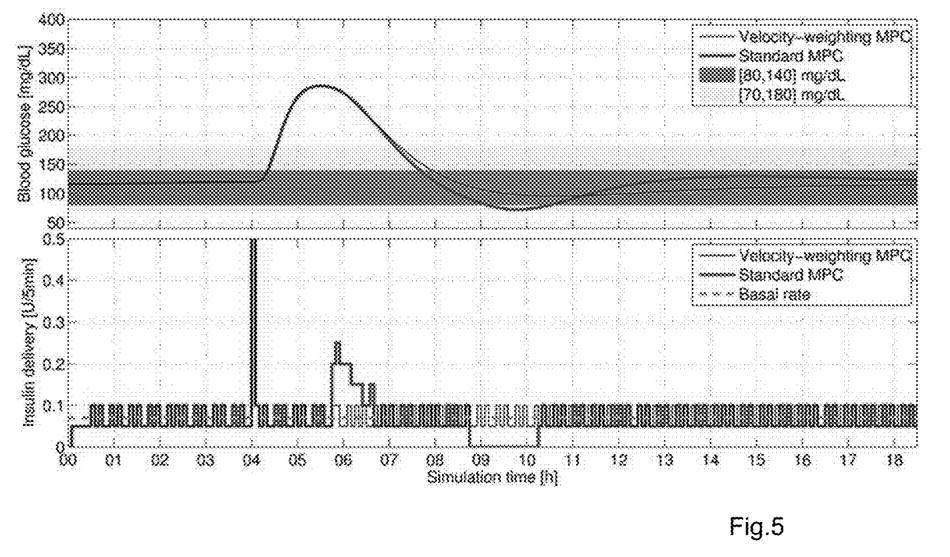
FIG. 5. Announced meal. In-silico subject #13 of 100.

The examples above had unannounced meals, but the proposed velocity-weighting reduces the risk of hypoglycemia also with announced meals. In the example of FIG. 5 the IOB constraint prevents the controller from delivering more than the basal-rate until 05:45, due to the meal-bolus delivered at 04:00. After 05:45, during the glucose descent, standard MPC delivers in excess of the basal rate, and hypoglycemia is induced at 09:45, with an associated pump-suspension and subsequent glucose rebound. In contrast, the disclosed velocity-weighting MPC continuously delivers close to the basal-rate following the meal-bolus, despite the relaxing IOB constraint after 05:45, and no hypoglycemia is induced.

C. Comment on IOB Constraint Tuning

There is a trade-off to be made when tuning the IOB constraint mechanism based on the decay curves depicted in FIG. 1. On the one hand, a longer decay curve results in less insulin delivery, because delivered insulin is modeled to be active for longer, and so, following a meal-bolus, it takes longer before the controller is given leeway to attempt correcting hyperglycemia. For standard MPC and the case of FIG. 5, the use of longer decay curves would have prevented controller-induced hypoglycemia. On the other hand, in general it is desirable to allow the controller more leeway to control hyperglycemia. The use of the proposed velocity-weighting MPC partially alleviates this trade-off: One can employ shorter decay curves, giving the controller more leeway to control rising or persistently high glucose values early after a meal-bolus, while enforcing that insulin delivery is not excessive when glucose values are falling due to the delayed action of the meal-bolus.

D. Population Results

Figure 6:
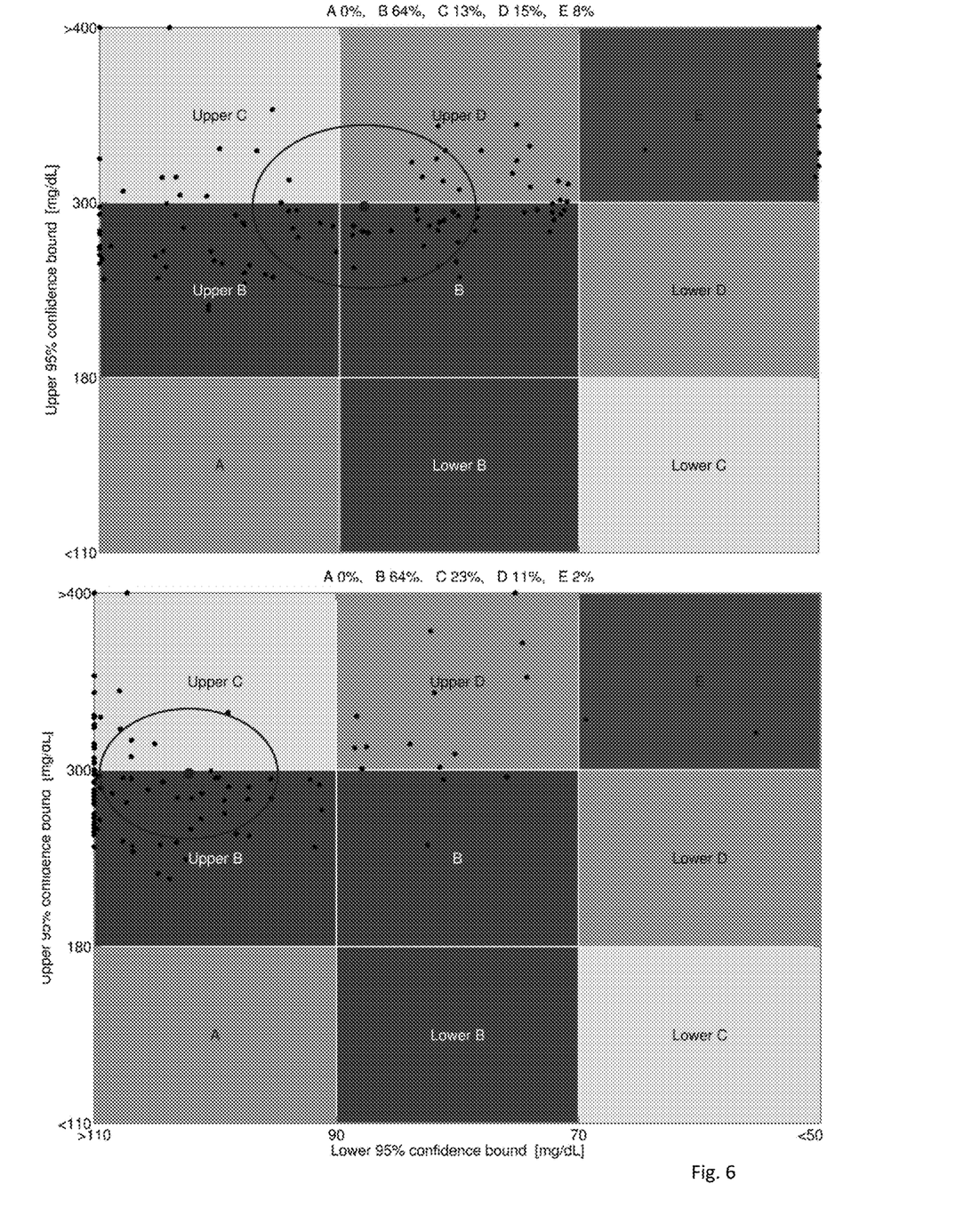
FIG. 6. Unannounced meal. Top: Standard MPC. Bottom: Proposed velocity-weighting MPC. For zone counts and cluster circle radii see Table I.
Figure 7:
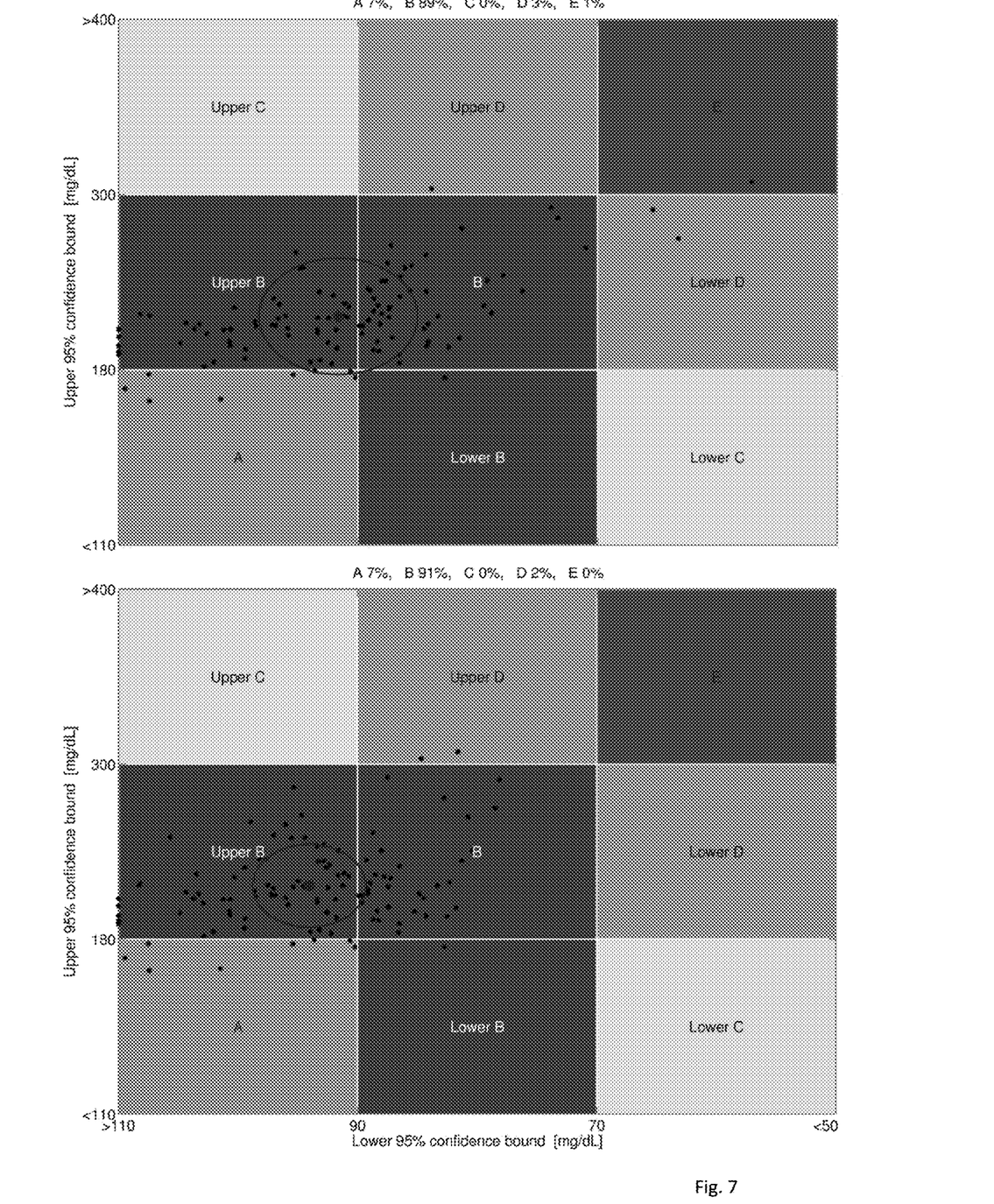
FIG. 7. Announced meal. Top: Standard MPC. Bottom: Proposed velocity-weighting MPC. For zone counts and cluster circle radii see Table I.

We consider Control Variability Grid Analysis (CVGA) [22] of the entire cohort in the University of Padova/Virginia metabolic simulator, consisting of 10-subject and 100-subject simulator cohorts. The latter contains a 101st subject "average", resulting in a combined cohort of 111 in-silico subjects. The CVGA plots for unannounced and announced meals are depicted in FIGS. 6 and 7, respectively. Top sub-plots show the results with standard MPC; bottom sub-plots are for the proposed velocity-weighting MPC. Each in-silico subject's result is denoted by a black dot. The large blue dot is the arithmetic mean of the individual dots, and the blue circle has a radius of the standard deviation of the distances of each dot to the cohort's mean, each in terms of the underlying CVGA space. The circles' radii, and also the CVGA zone inclusion percentages, are tabulated in Table I.

TABLE I

CVGA zone (A, . . . , E) inclusion percentages, and cluster circle radii [mg/dL], of the four cases depicted in FIGS. 6 and 7.

| Meal-type | MPC | A | B | C | D | E | Radius |
|---|---|---|---|---|---|---|---|
| Unannounced | Standard | 0% | 64% | 13% | 15% | 8% | 9.3 |
| | Proposed | 0% | 64% | 23% | 11% | 2% | 7.4 |
| Announced | Standard | 7% | 89% | 0% | 3% | 1% | 6.6 |
| | Proposed | 7% | 91% | 0% | 2% | 0% | 4.7 |

Due to the lack of CGM noise and fixed R the glucose peak (vertical position) for each subject is equal for both MPC strategies. The MPC strategy affects only the depth of the nadir (horizontal position). For unannounced meals most subjects undergo a shift to the left, i.e., the nadir is higher, meaning the hypoglycemia risk is reduced. The average is significantly shifted to the left, and the spread is smaller. For announced meals the peaks are significantly lower, due to the feed-forward nature of the meal announcement. For many subjects there is no difference between standard MPC and the proposed velocity-weighting MPC. However, there is an overall shift to the left, the spread is less, and for a small number of subjects the use of velocity-weighting clearly alleviates a significant risk of controller-induced hypoglycemia.

IV. Conclusion

A velocity-weighting mechanism is disclosed for MPC of an AP, such that deviations of predicted blood-glucose values are penalized by a cost-function that takes into account both the size of the deviation and also the velocity of the trajectory the predicted glucose value is an element of. Thus the MPC cost-function is made more "velocity aware", and the AP's response during the uphill and downhill leg of a hyperglycemic excursion can be tailored somewhat independently. By simulation examples it was demonstrated that the risk of controller-induced hypoglycemia is alleviated by disclosed strategy, as per design objective.

REFERENCES

[1] H. Zisser, "Clinical Hurdles and Possible Solutions in the Implementation of Closed-Loop Control in Type 1 Diabetes Mellitus," J Diabetes Sci Technol, vol. 5, pp. 1283-1286, September 2011.

[2] C. Cobelli, E. Renard, and B. Kovatchev, "Artificial Pancreas: Past, Present, Future," Diabetes, vol. 60, pp. 2672-2682, November 2011.

[3] F. J. Doyle I I I, L. M. Huyett, J. B. Lee, H. C. Zisser, and E. Dassau, "Closed Loop Artificial Pancreas Systems: Engineering the Algorithms," Diabetes Care, vol. 37, pp. 1191-1197, May 2014.

[4] R. Hovorka, "Continuous glucose monitoring and closed-loop systems," Diabetic Med, vol. 23, pp. 1-12, January 2006.

[5] R. S. Parker, F. J. Doyle III, and N. A. Peppas, "A Model-Based Algorithm for Blood Glucose Control in Type I Diabetic Patients," IEEE Trans Biomed Eng, vol. 46, pp. 148-157, February 1999.

[6] R. Hovorka, V. Canonico, L. J. Chassin, U. Haueter, M. Massi-Benedetti, M. O. Federici, T. R. Pieber, H. C. Schaller, L. Schaupp, T. Vering, and M. E. Wilinska, "Nonlinear model predictive control of glucose concentration in subjects with type 1 diabetes," Physiol Meas, vol. 25, pp. 905-920, July 2004.

[7] L. Magni, D. M. Raimondo, C. Dalla Man, G. De Nicolao, B. Kovatchev, and C. Cobelli, "Model predictive control of glucose concentration in type 1 diabetic patients: An in silico trial," Biomed Signal Process Control, vol. 4, no. 4, pp. 338-346, 2009.

[8] M. Breton, A. Farret, D. Bruttomesso, S. Anderson, L. Magni, S. Patek, C. Dalla Man, J. Place, S. Demartini, S. Del Favero, C. Toffanin, C. Hughes-Karvetski, E. Dassau, H. Zisser, F. J. Doyle III, G. De Nicolao, A. Avogaro, C. Cobelli, E. Renard, and B. Kovatchev, "Fully Integrated Artificial Pancreas in Type 1 Diabetes: Modular Closed-Loop Glucose Control Maintains Near Normoglycemia," Diabetes, vol. 61, pp. 2230-2237, June 2012.

[9] K. Turksoy, E. S. Bayrak, L. Quinn, E. Littlejohn, and A. Cinar, "Multivariable Adaptive Closed-Loop Control of an Artificial Pancreas Without Meal and Activity Announcement," Diabetes Technol Ther, vol. 15, pp. 386-400, May 2013.

[10] G. M. Steil, K. Rebrin, C. Darwin, F. Hariri, and M. F. Saad, "Feasibility of Automating Insulin Delivery for the Treatment of Type 1 Diabetes," Diabetes, vol. 55, pp. 3344-3350, December 2006.

[11] G. Marchetti, M. Barolo, L. Jovanovic, H. Zisser, and D. E. Seborg, "A feedforward-feedback glucose control strategy for type 1 diabetes mellitus," J Process Control, vol. 18, pp. 149-162, February 2008.

[12] B. Grosman, E. Dassau, H. C. Zisser, L. Jovanovic, and F. J. Doyle III, "Zone Model Predictive Control: A Strategy to Minimize Hyper- and Hypoglycemic Events," J Diabetes Sci Technol, vol. 4, pp. 961-975, July 2010.

[13] K. van Heusden, E. Dassau, H. C. Zisser, D. E. Seborg, and F. J. Doyle III, "Control-Relevant Models for Glucose Control Using A Priori Patient Characteristics," IEEE Trans Biomed Eng, vol. 59, pp. 1839-1849, July 2012.

[14] R. Gondhalekar, E. Dassau, H. C. Zisser, and F. J. Doyle III, "Periodic-Zone Model Predictive Control for Diurnal Closed-loop Operation of an Artificial Pancreas," J Diabetes Sci Technol, vol. 7, pp. 1446-1460, November 2013.

[15] J. M. Maciejowski, Predictive Control with Constraints. Harlow, England: Pearson/Prentice Hall, 2002.

[16] J. B. Rawlings and D. Q. Mayne, Model Predictive Control: Theory and Design. Madison, Wis., USA: Nob Hill Publishing, August 2009.

[17] R. Gondhalekar, E. Dassau, and F. J. Doyle III, "MPC Design for Rapid Pump-Attenuation and Expedited Hyperglycemia Response to Treat T1DM with an Artificial Pancreas," in Proc AACC American Control Conf, (Portland, Oreg., USA), pp. 4224-4230, June 2014.

[18] J. Walsh and R. Roberts, Pumping Insulin. San Diego, Calif., USA: Torrey Pines Press, 4 ed., 2006.

[19] W. S. Levine, ed., The Control Handbook. Boca Raton, Fla., USA: CRC Press, 2 ed., 2011.

[020] C. Ellingsen, E. Dassau, H. Zisser, B. Grosman, M. W. Percival, L. Jovanovic, and F. J. Doyle III, "Safety Constraints in an Artificial Pancreatic beta Cell: An Implementation of Model Predictive Control with Insulin on Board," J Diabetes Sci Technol, vol. 3, pp. 536-544, May 2009.

[21] B. P. Kovatchev, M. Breton, C. Dalla Man, and C. Cobelli, "In Silico Preclinical Trials: A Proof of Concept in Closed-Loop Control of Type 1 Diabetes," J Diabetes Sci Technol, vol. 3, pp. 44-55, January 2009.

[22] L. Magni, D. M. Raimondo, C. Dalla Man, M. Breton, S. Patek, G. De Nicolao, C. Cobelli, and B. Kovatchev, "Evaluating the Efficacy of Closed-Loop Glucose Regulation via Control-Variability Grid Analysis," J Diabetes Sci Technol, vol. 2, pp. 630-635, July 2008.

[23] R. Gondhalekar, E. Dassau, F. J. Doyle III, Velocity-weighting to prevent controller-induced hypoglycemia in MPC of an artificial pancreas to treat T1DM, in Proc. AACC American Control Conf, (Chicago, Ill., USA), June 2015

What is claimed is:

1. A method of controlling insulin delivery comprising:
implementing a velocity-weighting mechanism in a model predictive control (MPC) cost function in operation of an insulin pump controller by penalizing predicted glucose outcomes with a cost modulated by a factor that is a function of glucose velocity, wherein the predicted glucose outcomes are penalized increasingly less for increasingly negative glucose velocities, when glucose level is high, and wherein a hyperglycemic glucose value that is already converging to a euglycemic zone results in less corrective action than were the hyperglycemic value steady, thereby independently shaping uphill versus downhill responses of the controller to hyperglycemic glucose excursions, wherein uphill and downhill are in reference to the glucose excursions, wherein uphill refers to increasing blood glucose, and downhill refers to decreasing blood glucose.

2. The method of claim 1, wherein the cost is defined by Q(v): wherein the Q(v) is 1 when the glucose velocity (v) is >0, the Q(v) is $\varepsilon \ll 1$ when v<−1, and the Q(v) is a smooth transition cost function that smoothly converges the cost to zero when: −1<v <0.

3. The method of claim 2, further comprising
predicting the glucose outcomes based on blood glucose measurements.

4. The method of claim 3, further comprising:
delivering insulin to a patient from a pump controlled by the controller implementing the velocity-weighting mechanism in the MPC cost function.

5. The method of claim 2, further comprising
measuring blood glucose with a continuous glucose monitor (CGM) sensor to obtain blood glucose measurements; and
predicting the glucose outcomes based on the blood glucose measurements.

6. The method of claim 5, further comprising:
delivering insulin to a patient from a pump controlled by the controller implementing the velocity-weighting mechanism in the MPC cost function.

7. The method of claim 2, further comprising:
delivering insulin to a patient from a pump controlled by the controller implementing the velocity-weighting mechanism in the MPC cost function.

8. The method of claim 1 wherein the cost is defined by Q(v): wherein the Q(v) is 1 when the glucose velocity (v) is >0, the Q(v) is $\varepsilon \ll 1$ when v<−1, and the Q(v) is a smooth transition cost function that smoothly converges the cost to zero when: −1<v <0, and wherein the smooth transition cost function is: $\frac{1}{2}[\cos(v\pi)(1-\varepsilon)+(1+\varepsilon)]$.

9. The method of claim 8, further comprising
predicting the glucose outcomes based on blood glucose measurements.

10. The method of claim 9, further comprising:
delivering insulin to a patient from a pump controlled by the controller implementing the velocity-weighting mechanism in the MPC cost function.

11. The method of claim 8, further comprising
measuring blood glucose with a continuous glucose monitor (CGM) sensor to obtain blood glucose measurements; and
predicting the glucose outcomes based on the blood glucose measurements.

12. The method of claim 11, further comprising:
delivering insulin to a patient from a pump controlled by the controller implementing the velocity-weighting mechanism in the MPC cost function.

13. The method of claim 8, further comprising:
delivering insulin to a patient from a pump controlled by the controller implementing the velocity-weighting mechanism in the MPC cost function.

14. The method of claim 1, further comprising
predicting the glucose outcomes based on blood glucose measurements.

15. The method of claim 14, further comprising:
delivering insulin to a patient from a pump controlled by the controller implementing the velocity-weighting mechanism in the MPC cost function.

16. The method of claim 1, further comprising
measuring blood glucose with a continuous glucose monitor (CGM) sensor to obtain blood glucose measurements; and
predicting the glucose outcomes based on the blood glucose measurements.

17. The method of claim 16, further comprising:
delivering insulin to a patient from a pump controlled by the controller implementing the velocity-weighting mechanism in the MPC cost function.

18. The method of claim 1, further comprising:
delivering insulin to a patient from a pump controlled by the controller implementing the velocity-weighting mechanism in the MPC cost function.

* * * * *